(12) United States Patent
DiFoggio

(10) Patent No.: US 8,032,311 B2
(45) Date of Patent: Oct. 4, 2011

(54) ESTIMATING GAS-OIL RATIO FROM OTHER PHYSICAL PROPERTIES

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 574 days.

(21) Appl. No.: 12/154,391

(22) Filed: May 22, 2008

(65) Prior Publication Data

US 2009/0292474 A1 Nov. 26, 2009

(51) Int. Cl.
*G01N 31/00* (2006.01)
(52) U.S. Cl. .................. 702/24; 702/9; 702/11; 702/12; 702/14; 702/22; 702/23; 702/25; 702/30; 702/35; 702/50; 702/66; 702/73; 702/79; 702/100; 702/116; 702/141; 702/168; 702/183; 250/256; 250/269.1; 73/152.04; 73/152.05; 73/152.08; 73/152.09
(58) Field of Classification Search ................ 702/9, 11, 702/12, 14, 22–25, 30, 35, 50, 66, 73, 79, 702/100, 116, 141, 168, 183; 250/256, 269.1; 73/152.04, 152.05, 152.08, 152.09
See application file for complete search history.

(56) References Cited

U.S. PATENT DOCUMENTS

| | | | |
|---|---|---|---|
| 4,439,497 A | 3/1984 | DiFoggio | |
| 4,587,641 A | 5/1986 | DiFoggio | |
| 4,746,210 A | 5/1988 | DiFoggio et al. | |
| 4,771,634 A | 9/1988 | DiFoggio | |
| 4,787,983 A | 11/1988 | DiFoggio et al. | |

(Continued)

FOREIGN PATENT DOCUMENTS

CN 1761868 A 4/2006
(Continued)

OTHER PUBLICATIONS

Benson et al. "A modeling solution for predicting (a) dry rock bulk modulus, rigidity modulus and (b) seismic velocities and reflection coefficient in porous, fluid-filled rocks with applications to laboratory rock samples and well logs," Nov. 1998.*

(Continued)

*Primary Examiner* — Sujoy Kundu
(74) *Attorney, Agent, or Firm* — Arnold & Knobloch, L.L.P.

(57) ABSTRACT

A method for characterizing a desired property of a fluid downhole is described. In some non-limiting examples, the method comprises receiving an input signal representing sound speed of a fluid downhole, processing the input signal using a correlation equation expressing the desired property in terms of at least sound speed to produce an output signal representing the desired property, and outputting the output signal. In some examples, the correlation equation is derived through a chemometric analysis of a training data set, the training data set comprises a plurality of input values and a plurality of output values derived from said input values, between the desired fluid property and the first measured property, and the output values are calculated from the input values using a series of correlation equations. In at least one example, the desired property is gas oil ratio. In another example, the desired property is gas brine ratio. In a further example, the series of correlation equations comprises the Batzle and Wang relations. In another example, the receiving comprises receiving a plurality of input signals representing a plurality of measured properties of a fluid downhole and the processing comprises processing the plurality of input signals using the correlation equation expressing the desired property in terms of the plurality of measured properties.

17 Claims, 5 Drawing Sheets

U.S. PATENT DOCUMENTS

| | | | |
|---|---|---|---|
| 4,866,983 A | 9/1989 | Vinegar et al. | |
| 4,920,792 A | 5/1990 | DiFoggio | |
| 5,114,567 A | 5/1992 | DiFoggio | |
| 5,166,910 A | 11/1992 | Batzle et al. | |
| 5,179,598 A | 1/1993 | DiFoggio et al. | |
| 5,212,353 A | 5/1993 | Rambow et al. | |
| 5,360,972 A | 11/1994 | DiFoggio et al. | |
| 5,397,899 A | 3/1995 | DiFoggio et al. | |
| 5,668,374 A | 9/1997 | DiFoggio et al. | |
| 5,984,009 A | 11/1999 | DiFoggio | |
| 6,218,662 B1 | 4/2001 | Tchakarov et al. | |
| 6,341,498 B1 | 1/2002 | DiFoggio | |
| 6,420,869 B1 | 7/2002 | DiFoggio | |
| 6,627,873 B2 | 9/2003 | Tchakarov et al. | |
| 6,672,093 B2 | 1/2004 | DiFoggio | |
| 6,683,681 B2 | 1/2004 | DiFoggio et al. | |
| 6,714,872 B2 | 3/2004 | DiFoggio et al. | |
| 6,798,518 B2 | 9/2004 | DiFoggio et al. | |
| 6,837,105 B1 | 1/2005 | DiFoggio et al. | |
| 6,877,332 B2 | 4/2005 | DiFoggio | |
| 6,907,797 B2 | 6/2005 | DiFoggio | |
| 6,938,470 B2 | 9/2005 | DiFoggio et al. | |
| 6,976,392 B2 | 12/2005 | DiFoggio et al. | |
| 6,997,055 B2 | 2/2006 | DiFoggio | |
| 7,016,026 B2 | 3/2006 | DiFoggio et al. | |
| 7,024,917 B2 | 4/2006 | DiFoggio | |
| 7,027,928 B2 | 4/2006 | DiFoggio | |
| 7,082,994 B2 | 8/2006 | Frost, Jr. et al. | |
| 7,084,392 B2 | 8/2006 | DiFoggio et al. | |
| 7,124,596 B2 | 10/2006 | DiFoggio et al. | |
| 7,162,918 B2 | 1/2007 | DiFoggio et al. | |
| 7,173,239 B2 | 2/2007 | DiFoggio | |
| 7,196,786 B2 | 3/2007 | DiFoggio | |
| 7,197,195 B2 | 3/2007 | DiFoggio et al. | |
| 7,214,933 B2 | 5/2007 | DiFoggio et al. | |
| 7,219,541 B2 | 5/2007 | DiFoggio | |
| 7,240,546 B2 | 7/2007 | DiFoggio | |
| 7,280,214 B2 | 10/2007 | DiFoggio et al. | |
| 7,299,136 B2 | 11/2007 | DiFoggio et al. | |
| 7,317,989 B2 | 1/2008 | DiFoggio et al. | |
| 7,346,460 B2 | 3/2008 | DiFoggio et al. | |
| 7,362,422 B2 | 4/2008 | DiFoggio et al. | |
| 7,373,813 B2 | 5/2008 | DiFoggio | |
| 7,387,021 B2 | 6/2008 | DiFoggio | |
| 7,395,704 B2 | 7/2008 | DiFoggio | |
| 7,408,645 B2 | 8/2008 | DiFoggio | |
| 2002/0043620 A1 | 4/2002 | Tchakarov et al. | |
| 2002/0104328 A1 | 8/2002 | DiFoggio | |
| 2002/0178805 A1 | 12/2002 | DiFoggio et al. | |
| 2003/0066359 A1* | 4/2003 | Gysling et al. | 73/861.23 |
| 2003/0085039 A1 | 5/2003 | DiFoggio | |
| 2003/0163259 A1 | 8/2003 | DiFoggio et al. | |
| 2003/0193662 A1 | 10/2003 | DiFoggio et al. | |
| 2003/0223068 A1 | 12/2003 | DiFoggio et al. | |
| 2003/0223069 A1 | 12/2003 | DiFoggio et al. | |
| 2004/0007665 A1 | 1/2004 | DiFoggio et al. | |
| 2004/0089448 A1 | 5/2004 | DiFoggio | |
| 2004/0104355 A1 | 6/2004 | DiFoggio et al. | |
| 2004/0109156 A1 | 6/2004 | DiFoggio et al. | |
| 2004/0178336 A1 | 9/2004 | DiFoggio | |
| 2004/0216521 A1 | 11/2004 | Shammai et al. | |
| 2004/0216873 A1 | 11/2004 | Frost, Jr. et al. | |
| 2004/0218176 A1 | 11/2004 | Shammai et al. | |
| 2004/0236512 A1 | 11/2004 | DiFoggio et al. | |
| 2004/0260497 A1 | 12/2004 | DiFoggio et al. | |
| 2005/0005624 A1 | 1/2005 | DiFoggio et al. | |
| 2005/0007583 A1 | 1/2005 | DiFoggio | |
| 2005/0018192 A1 | 1/2005 | DiFoggio et al. | |
| 2005/0094921 A1 | 5/2005 | DiFoggio et al. | |
| 2005/0099618 A1 | 5/2005 | DiFoggio et al. | |
| 2005/0109098 A1 | 5/2005 | DiFoggio | |
| 2005/0122839 A1 | 6/2005 | DiFoggio et al. | |
| 2005/0182566 A1 | 8/2005 | DiFoggio | |
| 2005/0204808 A1 | 9/2005 | DiFoggio | |
| 2005/0205256 A1 | 9/2005 | DiFoggio | |
| 2005/0246151 A1 | 11/2005 | DiFoggio | |
| 2005/0247119 A1 | 11/2005 | DiFoggio et al. | |
| 2005/0262936 A1 | 12/2005 | DiFoggio | |
| 2006/0032301 A1 | 2/2006 | DiFoggio | |
| 2006/0037385 A1 | 2/2006 | Gysling | |
| 2006/0139646 A1 | 6/2006 | DiFoggio | |
| 2006/0175547 A1 | 8/2006 | DiFoggio et al. | |
| 2006/0198742 A1 | 9/2006 | DiFoggio et al. | |
| 2006/0213660 A1 | 9/2006 | DiFoggio et al. | |
| 2006/0213669 A1 | 9/2006 | Shipley et al. | |
| 2006/0236758 A1 | 10/2006 | DiFoggio et al. | |
| 2006/0241866 A1 | 10/2006 | DiFoggio | |
| 2006/0266108 A1 | 11/2006 | DiFoggio | |
| 2006/0266109 A1 | 11/2006 | DiFoggio | |
| 2007/0013911 A1 | 1/2007 | DiFoggio | |
| 2007/0022803 A1 | 2/2007 | DiFoggio et al. | |
| 2007/0029197 A1 | 2/2007 | DiFoggio | |
| 2007/0034793 A1 | 2/2007 | Estes et al. | |
| 2007/0068242 A1 | 3/2007 | DiFoggio | |
| 2007/0081157 A1 | 4/2007 | Csutak et al. | |
| 2007/0095096 A1 | 5/2007 | DiFoggio | |
| 2007/0095535 A1 | 5/2007 | DiFoggio et al. | |
| 2007/0113639 A1 | 5/2007 | DiFoggio et al. | |
| 2007/0120051 A1 | 5/2007 | DiFoggio et al. | |
| 2007/0129901 A1 | 6/2007 | DiFoggio et al. | |
| 2007/0159625 A1 | 7/2007 | DiFoggio | |
| 2007/0193351 A1 | 8/2007 | DiFoggio | |
| 2007/0227241 A1 | 10/2007 | DiFoggio | |
| 2007/0238180 A1 | 10/2007 | DiFoggio et al. | |
| 2007/0251296 A1 | 11/2007 | DiFoggio | |
| 2007/0284099 A1 | 12/2007 | DiFoggio et al. | |
| 2008/0030729 A1 | 2/2008 | DiFoggio | |
| 2008/0047337 A1 | 2/2008 | Chemali et al. | |
| 2008/0149348 A1 | 6/2008 | DiFoggio et al. | |
| 2008/0163680 A1 | 7/2008 | DiFoggio | |
| 2008/0165356 A1 | 7/2008 | DiFoggio et al. | |

FOREIGN PATENT DOCUMENTS

| | | |
|---|---|---|
| EP | 1865147 A1 | 12/2007 |
| GB | 2217838 A | 11/1989 |
| WO | WO03102372 A1 | 12/2003 |
| WO | WO03102520 A1 | 12/2003 |
| WO | WO2004083833 | 9/2004 |

OTHER PUBLICATIONS

Batzle and Wang, "Seismic Properties of Pore Fluids," Geophysics, v.57, No. 11, pp. 1396-1408, Nov. 1992.

Hans and Batzle, "Velocity, Density and Modulus of Hydrocarbon Fluids—Data Measurement," Society of Exploration Geophysicists Technical Program, Expanded Abstracts, 2000, pp. 1862-1866, doi: 10.1190/1.1815792.

M.A. Sharaf, D.L. Illman and B.R.. Kowalski, Chemometrics, p. 126-127, John Wiley & Sons, New York, 1986. pp. 126-127.

http://www.itl.nist.gov/div898/handbook/pri/section3/pri3.htm.

Vidar Aseng, "Compressibility and Sound Speed," Diploma Thesis, Norwegian University of Science and Technology, Department of Petroleum Engineering and Applied Geophysics, pp. 1-44, Feb. 2006.

Terra E. Bulloch, "The Investigation of Fluid Properties and Seismic Attributes for Reservoir Characterization," Diploma Thesis, Michigan Technological University, Department of Geological Engineering and Sciences, 1999.

B.H. Russel, K. Hedlin, F.J. Hilterman, & L.R. Lines, "Fluid-Property Discrimination with AVO: A Biot-Gassmann Perspective," CREWES Research Report, pp. 403-419, vol. 13, 2001.

PCT Notification of Transmittal of the International Search Report and the Written Opinion of the International Searching Authority, or the Declaration, PCT/US08/64647, May 23, 2008.

Norman R. Draper and Harry Smith, Applied Regression Analysis, Third Edition, pp. 135-140, John Wiley & Sons, Inc., Wiley Interscience Publication.

* cited by examiner

| T | P | $\rho_0$ | G | $R_G$ | $B_0$ | $\rho'$ | $V'$ | log(V) | ... | $V'^2$ |
|---|---|---|---|---|---|---|---|---|---|---|
| #.#### | ##.#### | ##.#### | ##.#### | ##.#### | ##.#### | ##.#### | ##.#### | ##.#### | ... | ##.#### |
| #.#### | ##.#### | ##.#### | ##.#### | ##.#### | ##.#### | ##.#### | ##.#### | ##.#### | ... | ##.#### |
| #.#### | ##.#### | ##.#### | ##.#### | ##.#### | ##.#### | ##.#### | ##.#### | ##.#### | ... | ##.#### |
| ... | ... | ... | ... | ... | ... | ... | ... | ... | ... | ... |
| #.#### | ##.#### | ##.#### | ##.#### | ##.#### | ##.#### | ##.#### | ##.#### | ##.#### | ... | ##.#### |
| #.#### | ##.#### | ##.#### | ##.#### | ##.#### | ##.#### | ##.#### | ##.#### | ##.#### | ... | ##.#### |
| #.#### | ##.#### | ##.#### | ##.#### | ##.#### | ##.#### | ##.#### | ##.#### | ##.#### | ... | ##.#### |

- T, P: MEASURABLE DOWNHOLE
- $\rho_0$, G, $R_G$, $B_0$: UNMEASURABLE DOWNHOLE
- $\rho'$, $V'$: MEASURABLE DOWNHOLE
- log(V), ..., $V'^2$: ADDITIONAL PERMUTATIONS (OPTIONAL)
- T, P, $\rho_0$, G, $R_G$, $B_0$: INPUT VALUES
- $\rho'$, $V'$, log(V), ..., $V'^2$: CALCULATED VALUES

FIG. 3

ESTIMATING GAS-OIL RATIO FROM OTHER PHYSICAL PROPERTIES

FIELD OF THE INVENTION

The present invention relates generally to hydrocarbon exploration and production, and more particularly relates to a method and system for characterizing a desired property of a fluid downhole.

BACKGROUND OF THE INVENTION

This application is entitled to the benefit of the filing date of U.S. Provisional Patent Application No. 60/931,381 for "Estimating gas-oil ratio from other physical properties," filed May 23, 2007. Knowing the gas-oil ratio (GOR) of crude oil formations is of considerable interest to those involved in the exploration and production of hydrocarbons (oil and gas). Various methods for estimating GOR of a fluid downhole based on performing infrared spectroscopy are already well known in the art. GOR is typically characterized in terms of a number of standard cubic feet of gas per stock tank barrel of oil. For black oils, GOR is typically less than 2000 standard cubic feet of gas per stock tank barrel of oil. For volatile oils, GOR is typically between 2000 and 3300 standard cubic feet of gas per stock tank barrel of oil. Gas and oil density and modulus, as well as oil viscosity, increase with molecular weight and pressure, and decrease with temperature. Gas viscosity has a similar behavior, except at higher temperatures and lower pressures, where the viscosity will increase slightly with increasing temperature. Large amounts of gas go into solution in lighter oils and substantially lower the modulus and viscosity.

Brine modulus, density, and viscosities increase with increasing salt content and pressure. Brine is peculiar because the modulus reaches a maximum at a temperature from 40 to 80° C. Far less gas can be absorbed by brines than by light oils. As a result, gas in solution in oils can drive their modulus so far below that of brines that seismic reflection "bright spots" may develop from the interface between the oil-saturated and brine-saturated rocks.

A prior reference of particular note with respect to pore fluids is Batzle and Wang, "Seismic Properties of Fluids," *Geophysics*, v. 57, no. 11, pp. 1396-1408 (November, 1992) (hereinafter, "Batzle and Wang," which is hereby incorporated by reference herein in its entirety for all purposes). The teachings of Batzle and Wang, commonly and collectively referred to as the Batzle and Wang relations, are widely known to and used by those of ordinary skill in the art.

In general terms, the Batzle and Wang relations comprise a series of separate correlation equations for sound speed and for GOR in terms of other parameters but it does not provide any equation for GOR in terms of sound speed, live oil density, pressure, and temperature. For example, one Batzle and Wang correlation equation relates gas-containing ("live") oil density to GOR, gas density, and formation volume factor. Another Batzle and Wang correlation equation relates formation volume factor to GOR, gas density, stock-tank ("dead") oil density, and temperature. The sound speed of live oil can be estimated by substituting for dead-oil density a pseudo-density based on expansion caused by gas intake into the equation for sound speed of dead oil. The sound speed of live oil at borehole temperatures and pressures is generally between 1100 and 1700 meters per second. Still another Batzle and Wang correlation equation relates the pseudo-density to formation volume factor, GOR, and stock-tank oil density.

Another reference, Han and Batzle, Velocity, Density and Modulus of Hydrocarbon Fluids—Data Measurement," *Society of Exploration Geophysicists Technical Program*, Expanded Abstracts, 2000, pp. 1862-1866, doi:10.1190/1.1815792 (hereinafter, "Han and Batzle," which is hereby incorporated by reference herein in its entirety for all purposes) elaborates on the Batzle and Wang formulations and is similarly widely known in the art.

While the utility of the Batzle and Wang approach to pore fluid characterization and the seismic significance of fluid and rock properties is widely recognized, there remain perceived shortcomings to such an approach, inasmuch as the suite of equations commonly ascribed to Batzle and Wang cannot be algebraically solved simultaneously to derive GOR values from sound speed, live oil density, pressure, and temperature because of their complexity. It is well-known to those of ordinary skill in the art that the roots of fifth-order or higher polynomials cannot in general be solved in terms of simple algebraic functions. This poses certain undesirable limitations on the practical utility of the prior art for this purpose of this invention as exemplified by Batzle and Wang and its progeny. For example, Batzle and Wang express GOR in terms of stock tank oil density and other parameters, which cannot be measured downhole.

In particular, it has heretofore not been shown a feasible methodology for characterizing the gas-oil ratios of a fluid downhole in terms of parameters, such as sound speed and live oil density, which are measurable downhole.

SUMMARY OF THE INVENTION

In view of the foregoing, the present invention relates to characterizing properties of fluids downhole. In at least one example of the invention the characterization is performed by taking a signal representing a measured property, or properties, of the downhole fluids and analyzing the desired property, or properties, and processing that signal using a correlation equation expressing the desired property in terms of the measured property, or properties, to produce an output signal representing the desired property. In many examples, the correlation equation is derived through a chemometric analysis of a training data set using a series of algebraically-unsolvable, simultaneous, crude-oil correlation equations, and in particular, to the assessment of gas-oil ratios, gas brine ratios, and other properties of fluids in hydrocarbon formations not typically measured downhole. Those of ordinary skill in the art will understand that chemometrics is the application of mathematical, statistical, graphical, and/or symbolic methods to chemical data to maximize the amount of information that can be derived therefrom. See, e.g., M. A. Sharaf, D. L. Illman and B. R. Kowalski, *Chemometrics*, John Wiley & Sons, New York, 1986 (which is hereby incorporated by reference herein in its entirety for all purposes). "Characterization" and/or "assessment" are general terms that encompass any measurement, calculation, estimation, grading, or relative grading of a property. The chemometric solution is an algebraic equation that approximates the relationship between different output parameters over some range of input parameters analogous to the way in which a Taylor series expansion approximates an arbitrary function in the neighborhood of a point of expansion. This approach provides the option of estimating GOR of a fluid downhole by using non-optical measurements.

In at least one specific embodiment, a method is provided that comprises: receiving at least one input signal representing sound speed of a fluid downhole; processing the input signal using the correlation equation expressing the desired property in terms of at least sound speed wherein an output signal representing the desired property is produced; and outputting the output signal.

In at least one embodiment, certain correlation equations relating to geophysical properties of a formation, such as those of Batzle and Wang (and others) are first used to create a synthetic training set. That is, a sound speed and GOR pair is calculated from a set of randomly-generated stock-tank oil density, pressure, temperature, formation volume factor, and gas density values ranging between expected minimum and maximum values for each property. It is to be noted that the properties used in generating the synthetic training set include those that cannot be measured downhole using currently available techniques and/or instrumentation. For example, to measure stock-tank oil density would require, first, separating gas from the crude oil and then measuring the resulting liquid density at 1 atmosphere and 60° Fahrenheit, which cannot be done in the high-temperature, high-pressure, downhole environment.

Also, note that the input values do not have to be generated randomly; in many examples, they may be generated by any of the standard methods of experimental design (e.g. factorial design, Plackett-Burman design, or Box-Behnken design (http://www.itl.nist.gov/div898/handbook/pri/section3/pri3.htm)). The purpose of any design is to make sure that every neighborhood of input value space is included so that each combination of input values, within the range of each property, is represented.

For lab experiments, experimental design is a valuable way to maximize the amount of information obtained while using the fewest number of costly lab experiments. Random design is generally too costly for lab experiments. However, for synthetic data generation, random design is not too costly because fast computers make it the easiest and most straightforward design to implement even for 10,000 synthetic samples.

In accordance with still a further example of the invention, a regression method is used to model the GOR relative to properties that are commonly measurable downhole, such as sound speed, temperature, pressure, live oil density, and so on, to create a correlation equation for GOR based on data that was generated synthetically from the original correlation equations. In various examples of the invention, the regression is performed through statistical and/or neural network methods.

BRIEF DESCRIPTION OF THE DRAWINGS

The foregoing and other features and aspects of the present invention will be best appreciated by reference to a detailed description of the specific embodiments of the invention, when read in conjunction with the accompanying drawings, wherein:

FIG. 3 illustrates the generation of a table of output data from input data. The columns of this table, along with various functions of the columns of this table (e.g., pressure squared, pressure cubed, reciprocal pressure, pressure times temperature, etc.), are then regressed against each other to develop a desired chemometric model/equation.

DETAILED DESCRIPTION OF A SPECIFIC EMBODIMENT OF THE INVENTION

In the disclosure that follows, in the interest of clarity, not all features of actual implementations are described. It will of course be appreciated that in the development of any such actual implementation, as in any such project, numerous engineering and technical decisions and selections must be made to achieve specific goals, while operating within the various known constraints that may be posed, which will vary from one implementation to another. Moreover, it is necessary to adhere to proper engineering and development practices for the environment in question. It will be appreciated that such development efforts might be complex and time-consuming, but would nevertheless be a routine undertaking for those of ordinary skill in the relevant fields.

Figure 1:
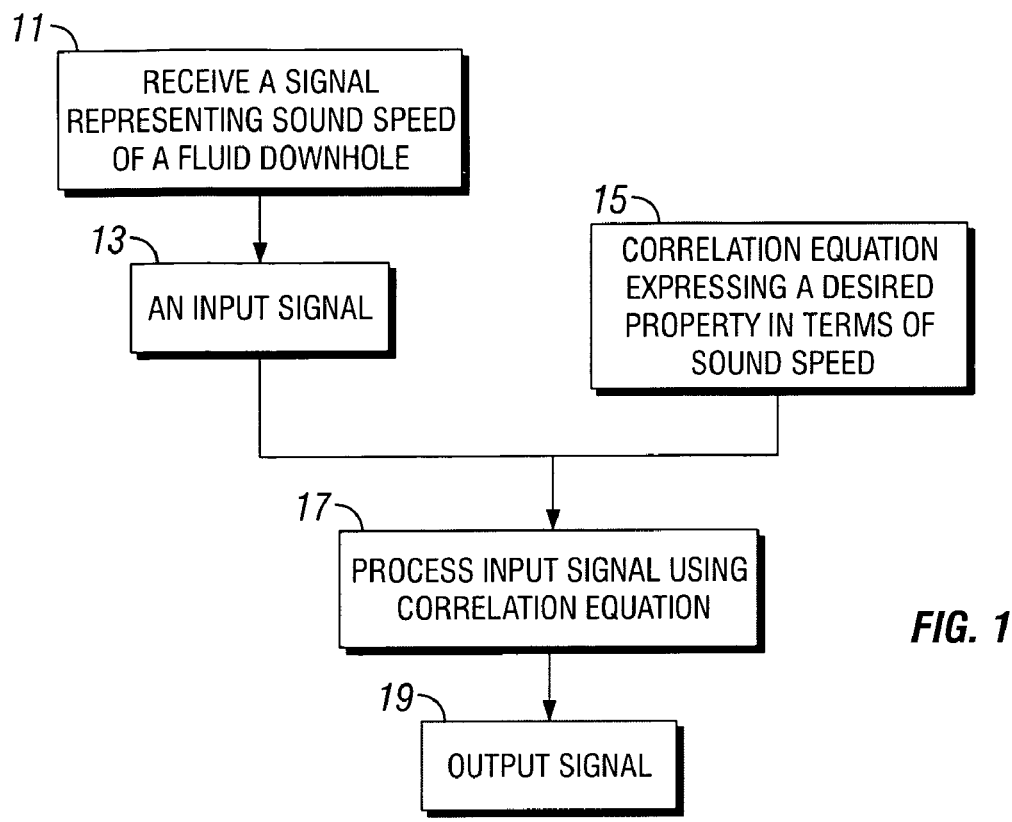
FIG. 1 is a flow diagram illustrating a method for characterizing a desired property of a fluid downhole by receiving a signal representing measuring sound speed of a fluid downhole and analyzing the desired property using a correlation equation expressing the desired property in terms of the measured properties in accordance with one embodiment of the invention.

Referring to FIG. 1, there is shown a flow diagram illustrating a method for characterizing a desired property of a fluid downhole in accordance with one example of the invention. As shown in FIG. 1, the process begins with step 11, receiving an input signal 13 representing sound speed of a fluid downhole. In one example of the invention the input signal is processed 17 using a correlation equation 15 expressing the desired property in terms of at least the sound speed.

Figure 2:
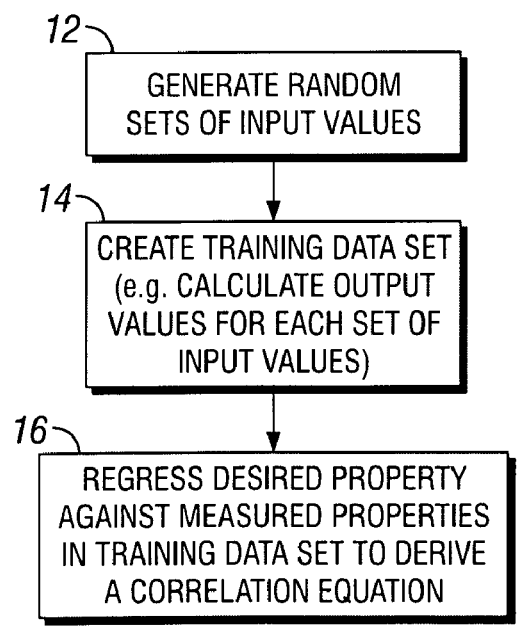
FIG. 2 is a flow diagram illustrating a chemometric methodology for deriving a correlation equation expressing a desired property in terms of a set of measured properties in accordance with one embodiment of the invention.

Referring to FIG. 2, there is shown a flow diagram illustrating a methodology for deriving a correlation equation expressing a desired property as a function of the set of measured fluid properties in accordance with one example of the invention. As shown in FIG. 2, a process begins with step 12 of generating sets of input parameter values.

In some examples of the invention, step 12 involves selection of a first plurality of input parameters whose values can be used to calculate the values of a second plurality of parameters. In at least one such embodiment, the input parameters include temperature (T), pressure (P), stock tank oil density ($\rho_0$), and gas gravity (G). Further, step 12 involves generating a plurality of (possibly random) combinations of values of these input variables. For each parameter, the random value is taken from a predetermined range within which that parameter can realistically and foreseeably be expected to lie in an actual subsurface environment. Thus, for example, the random values of temperature may be temperatures within the range $100° \leq T \leq 400°$ F. Pressure may be assumed to range from $0 \leq P \leq 30,000$ PSI.

For stock tank oil density, i.e., the density at room temperature and temperature of the "dead" oil after the entrained gas has escaped, a range of $0.60 \leq \rho_0 \leq 1.08$ grams per cubic centimeter is deemed to be a range that would be found reasonable to persons of ordinary skill in the art.

In one example, it is proposed to use an estimated value G=0.5556 for the gas gravity parameter, which represents a reasonable assumption that the gas is pure methane, which has a density approximately one-half the density of air. This value for G is reasonable because, by weight percent, natural gas averages about 86% methane and by mole percent, natural gas averages about 93% methane (Gas Research Institute Report # 82/0037). One could, of course, use slightly larger values for G to improve the model for heavier natural gases that contain more ethane, propane, butane, and so on.

Batzle and Wang proposes an equation for the saturation gas oil ratio $R_G$ as a function of the foregoing four variables T, P, G, and $\rho_0$, as follows:

Batzle and Wang further proposes an equation for the formation volume factor $B_0$ as a function of T, G, $\rho_0$, and $R_G$, each of which being available as set forth above. The formation volume factor equation is:

Batzle and Wang still further proposes an equation for the live oil density $\rho'$ in terms of $B_0$, $\rho_0$, and $R_G$, where again, each of these values is available as set forth above. In particular, Finally, Batzle and Wang proposes an approximation of live oil sound speed V' in terms of T, P, and $\rho_0$, and further suggests that substituting the live oil density $\rho'$ for the stock tank oil density $\rho_0$ for the equation for dead oil sound speed V to result in an acceptable approximation for the live oil sound speed V', such that:

Thus, for any given random combination of variables T, P, G, and $\rho_0$, one is able to generate a table such as that shown in FIG. 3. It is to be noted as shown in FIG. 3 that certain of the input values are measured (or measurable) using downhole instrumentation, while others are not measured (or measurable) using downhole instrumentation. Further, certain of the output values are measured/measurable downhole while others are not. "Measured/measurable downhole" is intended herein to refer to parameters whose values are commonly sensed by downhole instruments, whereas "not measured/measurable downhole" is intended to refer to properties that are not in a practical sense measurable using downhole instruments. These designations are not to be taken as absolute, as it is possible that technologies may be presently available or may be developed in the future for measuring properties designated as "not measurable." These designations are intended merely to reflect practical considerations as presently regarded by the inventor, and to highlight the versatility of the invention to account for the practical inability to measure (or undesirability of measuring) certain properties using downhole instrumentation.

The number of rows in the table of FIG. 3 corresponds to the number of sets of (possibly but not necessarily random) input values (the number of "samples" or "cases") included in the training data set. Those of ordinary skill in the art will appreciate that a larger number of samples will tend to improve the precision of results achieved in the practice of the present invention.

Referring again to FIG. 2, following the creation of the training data set in step 14, one embodiment next calls for performing a chemometric analysis of a desired property (i.e., a desired column from the table of FIG. 3) against other properties represented in FIG. 3. To achieve the maximum benefit of the invention, the desired property for which a regression is performed is preferably a property that is not readily measurable downhole, whereas the properties against which the regression is performed are preferably those that are readily measurable downhole and/or approximated by other means.

Performing a regression as called for in step 16 can be performed by any of numerous means and techniques well known to persons of ordinary skill in the art. In one embodiment, the regression is performed using STATISTICA™, an analytics software application commercially available from StatSoft®, Inc., Tulsa, Okla. STATISTICA™ is an analytical tool widely known and used by persons of ordinary skill in the art, and although this is a tool presently known to be suitable for the purposes of the present invention, it is to be understood that other tools or techniques, presently known or yet to be developed, may be utilized in the practice of the invention with equal efficacy. In another example of the invention the chemometric analysis can be performed by a neural network analysis.

Figure 4:
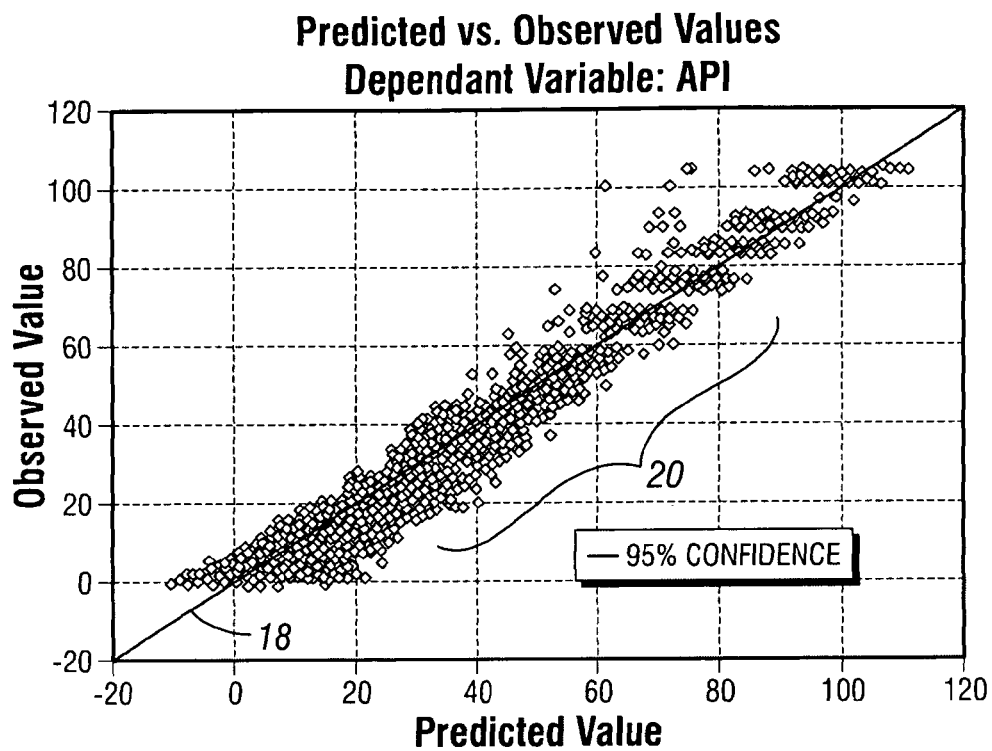
FIGS. 4 and 5 illustrate the fit of the chemometric models calculated from sound speed, density, temperature, and pressure. Those of ordinary skill will understand that the better that the chemometric model fits the simultaneous Batzle equations from which the synthetic data were derived, the closer that the points will be to the equal-value (perfect prediction) line.

Referring to FIG. 4, there is shown a plot graphically summarizing a regression process as performed in accordance with the presently disclosed embodiment. In particular, the plot of FIG. 4 is an example in which dependent variable API gravity (effectively an "inverse density") is regressed against live oil density $\rho'$, pressure P, and temperature (T). In FIG. 4, the substantially linear plot 18 represents the API values predicted using the Batzle and Wang equations, while the individual data points 20 in FIG. 4 represent API values computed using the regression model generated in accordance with the presently disclosed embodiment.

Analysis of the regression of FIG. 3 shows that the present invention achieves a high correlation coefficient $R^2=0.9799$ based on a synthetic training set comprising 6113 samples.

The result of the regression represented in FIG. 4 is expressed by the following equation for the American Petroleum Institute (API) oil gravity number:

As is known, this formula results in API values of less than ten for very heavy oils to near one hundred for light condensates. The API gravity is 10 for a liquid with the same density as water.

Figure 5:
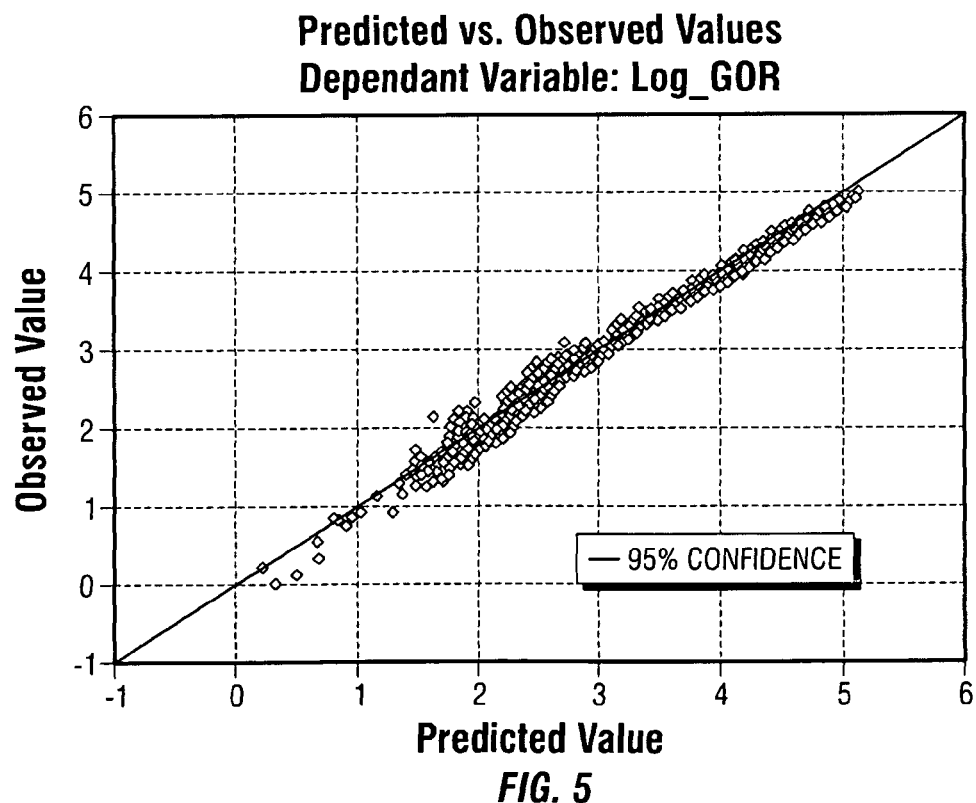

Turning to FIG. 5, there is shown a plot graphically summarizing another regression process as performed in accordance with an example embodiment. In this instance the dependent variable is the gas-oil ratio (GOR) is regressed against sound speed with 10702 samples. As can be seen in FIG. 5, the data values generated in accordance with the presently disclosed embodiment correlate to a very high degree with the values calculated using the Batzle and Wang equations (in particular, a correlation coefficient $R^2=0.9952$ is achieved).

In one example embodiment, a desired property of a fluid downhole is characterized through the use of a correlation equation expresssing the desired property in terms of fluid properties measured downhole. In one such example, the measured properties of the downhole fluid include sound speed measured downhole by generating an external acoustic signal, measuring the signal travel time through the fluid, and determining the fluid sound speed based on the measured travel time of the acoustic signal over a known distance through the fluid. Such a method for determining sound speed of a downhole fluid is described in more detail in U.S. patent application Ser. Nos. 11/194,365 by DiFoggio and Yao and 11/638,893 by DiFoggio, Bergren, and Han, incorporated herein by reference in its entirety for all purposes. The steps of this example method include measuring a set of fluid properties downhole and inputting the set of measured properties into a correlation equation expressing the desired property in terms of the measured fluid properties. The correlation equation is derived as explained in various examples herein.

Figure 6:
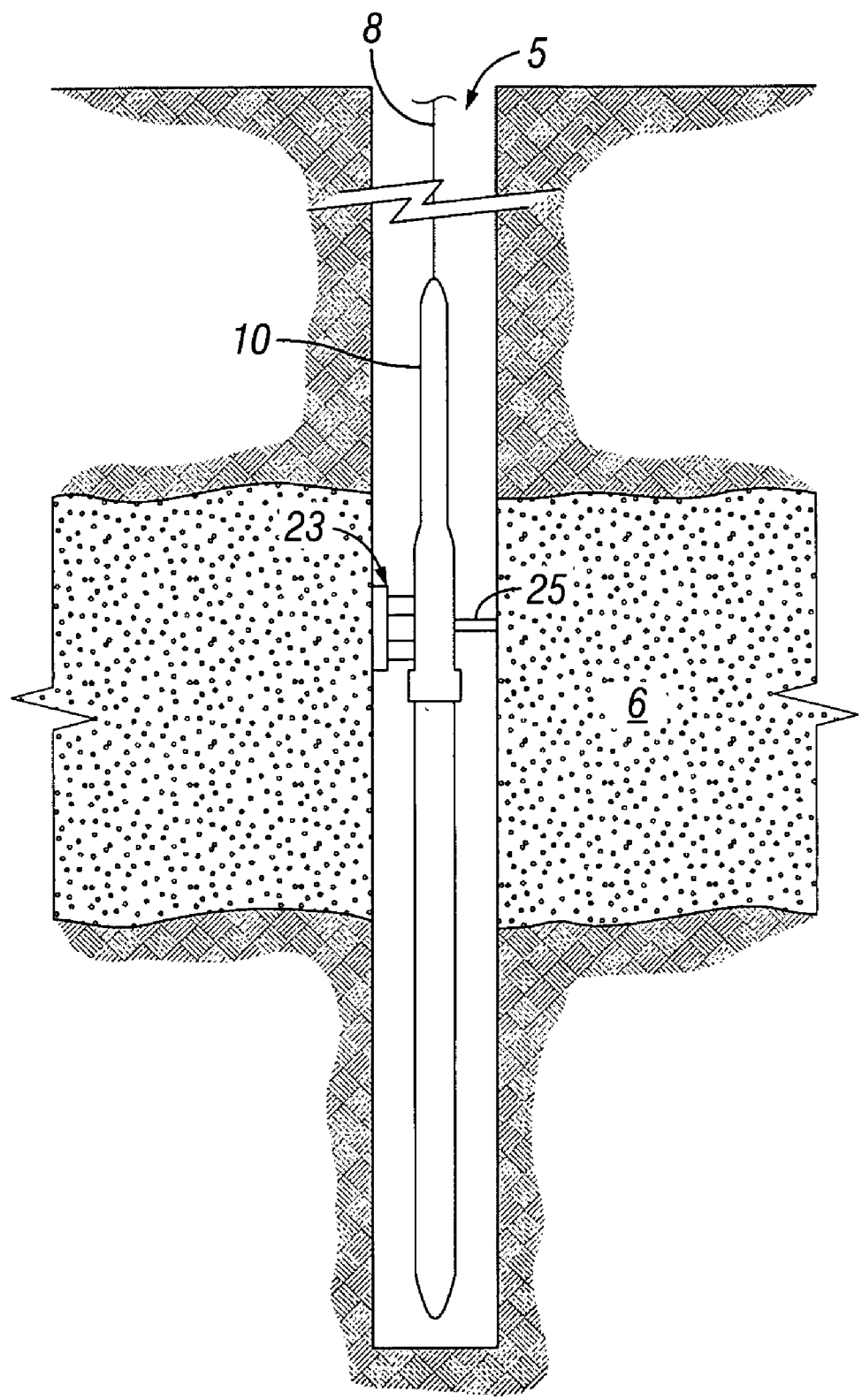
FIG. 6 portrays a sampling sonde disposed in a cut-away of a wellbore.
Figure 7:
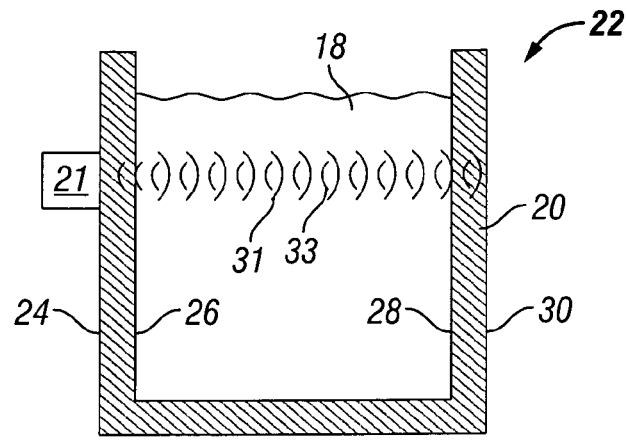
FIG. 7 illustrates a cut-away view of a sampling system.

With reference now to FIGS. 6 and 7, an embodiment of a sampling system 22 of an example device for measuring sound speed of a fluid downhole is illustrated in a partial cut-away view. The sampling system 22 of FIG. 5 comprises a vessel or container 20 in cooperation with a signal generator 21. The outer surface of the container 20 can have a radial or rectangular configuration as well as the shape of a tube. Optionally the vessel or container 20 can be comprised of a conduit or pipe.

As shown, the container 20 should be capable of retaining and storing the fluid 18 within its confines during analysis. Although shown as open at its top, the container 20 can also be sealed thereby fully encapsulating the fluid 18 therein. The signal generator 21 can be attached to the outer or first wall 24 of the container 20 or maintained in place. As will be described herein below, for the purposes of reference, both the first and second walls (24, 26) shown adjacent to the signal generator 21 are shown as well as the third and fourth walls (28, 30) distal from the signal generator 21.

With respect to the signal generator 21, it can be comprised of any device capable of producing a recordable acoustic signal that passes through the fluid. This includes traditional acoustic devices such as piezoelectric devices, however other acoustic transducers can also be used to accomplish this function. For example, an Electro-Magnetic Acoustic Transducer (EMAT) can insert ultrasonic waves into metal by electromagnetic coupling. Alternatively, a pulsed laser that strikes an object can generate acoustic waves at a frequency that depends on the laser pulse frequency; Moreover, the signal generator 21 can also be used as a receiver for receiving and recording reflections of the signals generated by the signal generator 21. One example of a flexural mechanical resonator useful with the device disclosed herein is described in detail in U.S. Pat. No. 6,938,470, the disclosure of which is incorporated for reference herein in its entirety for all purposes.

In one alternative of the present device, the sampling system 22 is combined with the sonde 10 and in fluid communication with the sample port 14. In this embodiment, connate fluid from the formation 6 is collected by the sample port 14 and delivered to the container 20 for analysis of the fluid. When used in conjunction with the sonde 10, the sampling system 22 is preferably housed within the sonde 10 during deployment and operation of the sampling system 22. Combining the sampling system 22 with the sonde 10 provides the advantage of "real time" sampling and reduces the risk of allowing changes in either the pressure or the temperature of the fluid that could in turn affect the sampling results. However, use of the sampling system 22 is not limited to the fluid collection apparatus of FIG. 1, but can be used with any type of device or circuit used in collecting downhole connate fluid.

In one non-limiting example of operation of the present method disclosed herein, connate fluid is drawn into the sample port 14 of a downhole sonde 10. The fluid is then introduced into the container 20 for subsequent analysis. The signal generator 21 is then activated so that a signal 31, such as one or more acoustic pulses, is generated. For the purposes of convenience the generated signal 31 is illustrated as a series of curved lines emanating from the transducer 21. After leaving the signal generator 21, the signal 31 passes through the first and second walls (24, 26) of the container 20, into the contained fluid 18, and onto the distal third and fourth walls (28, 30). A portion of the generated signal 31 (the reflected signal 33) reflects back to the direction of the signal generator 21. Similarly, the reflected signal 33 is illustrated for convenience as a series of curved lines directed towards the signal generator 21. In the embodiment of FIG. 2, the signal generator 21 can operate as a transmitter and also as a signal receiver. Optionally a separate transducer (not shown) could be included that operates solely as a signal receiver for receiving the reflected signals 33.

When the signal generator is a piezoelectric transducer, a short voltage spike can be applied to the transducer that typically lasts about 1-2 microseconds. This spike causes the transducer to resonate at its resonant frequency, which is typically from about 5 MHz to about 10 MHz. Analogous to a bell that rings for a while after it has been struck by a hammer, the transducer rings, primarily at its resonant frequency, for about a microsecond. An ever-decreasing portion of this microsecond-long pulse bounces back and forth between the tube wall that is bounded by surface 24 and surface 26, (which is in contact with the transducer 21) because a portion of the pulse is transmitted into the fluid upon each bounce off surface 26. The transmitted portion of the pulse passes beyond surface 26, enters the fluid 18, reflects from the surface 28, and eventually returns to be detected by the transducer 21. The acoustic transducer serves both as source and receiver. A high-speed (40-70 MHz) analog-to-digital converter monitors the signal received by the transducer.

As shown, the signal generator 21 receives and records the reflected signal for subsequent analysis. The recorded signal can either be immediately processed to determine fluid data, transmitted from the sonde 10 to a separate site for storage or data processing, or can be recorded within the sonde 10 for later analysis. As is known, the sound speed (c) of the liquid is determined by dividing the travel time of the signal through the fluid 18 by the distance the signal traveled through the fluid. This can be accomplished by designating the letter "d" as the distance between surface 26 and 28. Moreover, the variable 2t can be designated as the time difference between the arrival time of the first echo (corresponding to one round trip going from surface 24 to 26 and back again to 24) and the arrival time of the echo off surface 28 (corresponding to one round trip from 24, past 26, to 28, and eventually, back to 24). Therefore, 2t is amount of time it took sound to travel a round-trip distance, 2d, within the fluid from surface 26 to surface 28 and back to surface 26. The sound speed therefore is d/t.

In example method for measuring sound speed of a fluid downhole using the device described above, the raw amplitude data from the signal generator 21 can be first processed by applying a digital bandpass filter to reject any frequencies that are not close to the acoustic source frequency. For example, for a 10 MHz acoustic source and a 40 MHz sampling frequency, one could apply a 9-11 MHz digital bandpass filter. Next, one can compute the square of the amplitude at each sampling time, which corresponds to the energy received at that time. Then, one can generate a cumulative sum of squares (CSS) of these amplitudes, which is the cumulative sum of energy received up until that time. The digital bandpass filtering and cumulative sum of squares have already smoothed the raw data and removed some noise. We can further smooth the filtered cumulative sum of squares data and also take the first and second derivatives of the CSS using the Savitzky-Golay method (Savitzky and Golay, Analytical Chemistry, Vol. 36, No. 8, July 1964). The resulting data can be further processed by using a variable threshold method. Smoothing the data and the utilization of the Savitzky-Golay method help to reduce noise from the desired signal. The variable thresholding method serves to distinguish recorded signals emanating from the far wall of the vessel or container 20 from signals received that emanate from within the near wall (between surfaces 24 and 26) of the vessel or container 20.

Figure 8:
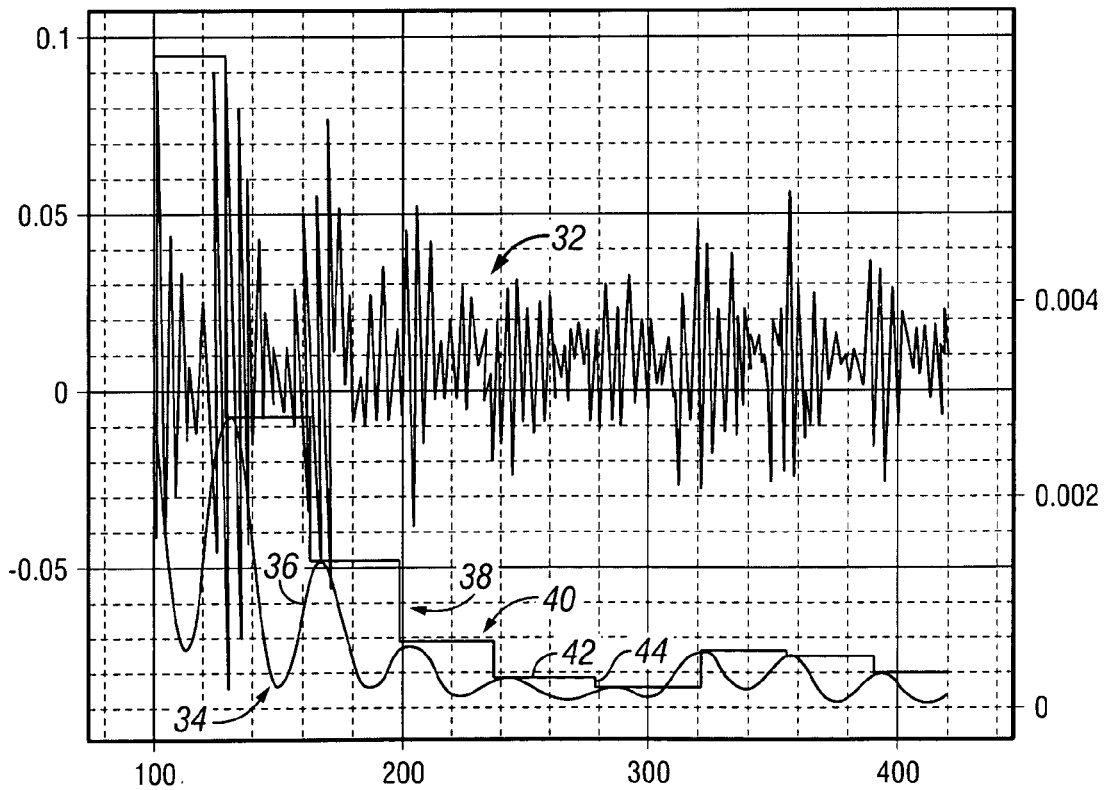
FIG. 8 represents plots containing raw data and processed data.

With reference now to FIG. 8, there is illustrated a plot having a raw data plot 32, a smooth data plot 34, and a variable threshold plot 38. In FIG. 8, the portion of the raw data has been redacted (as well as the corresponding smoothed and threshold data) that corresponds to the ringing of the transducer immediately after it receives a high voltage spike. This plot shows sampling of the signal amplitude at discrete intervals (digital data). To avoid aliasing, the sampling rate is several times the acoustic source frequency. After recording the data, the square of the amplitude for each channel is computed. The amplitude for each channel is proportional to the acoustic intensity (energy) that was received at that channel's time. Next, the cumulative sum (the "integral") of these squared amplitudes is calculated.

The data smoothing is further accomplished by computing the first derivative with respect to time of the cumulative sum of squares using Savitzky-Golay (SG) coefficients, which helps create smoothed numerical derivatives. Enhanced smoothing is accomplished by using Savitzky-Golay coefficients of lower order (such as square or cube) polynomials over a fairly large number of points (25 channels). The first derivative of the cumulative sum of squares is the smoothed energy received versus time, which shows distinct acoustic energy pulses. The resulting values produced by the Savitzky-Golay method are shown plotted in the smooth data plot 34 of FIG. 8.

In order to determine the local maxima and minima of the first derivative, the second derivative is taken of the cumulative sum of squares using Savitzky-Golay (SG) coefficients of a low order and a large number of points. The local maxima (pulse energy peaks) of the first derivative curve can be used to indicate the time at which a particular pulse reflection is received by the receiving transducer 21. It should be pointed out that the second derivative crosses zero when the first derivative reaches either its local maxima or minima. A pulse peak occurs between two channels whenever the second derivative changes from positive (in the left channel) to negative (in the right channel) with increasing time and the first derivative exceeds some variable threshold, which is described in detail later. Subchannel time resolution can be achieved by interpolating so as to estimate the location between two channels where the second derivative crosses zero. Alternatively, energy maxima can be distinguished from energy minima (both of which correspond to zeros of the second derivative of the CSS) based on the sign of the third derivative of the CSS.

Using the data obtained from the processed signal, the sound speed of the fluid within the vessel or container 20 is twice the wall thickness divided by the (round-trip) time between reverberation pulse peaks within the tube wall. The wall sound speed may change with temperature or with pressure of the fluid inside the tube thus causing the wall's acoustic impedance to change. The wall's acoustic impedance must be known to compute fluid density from fluid sound speed and the decay rate of within-wall pulse echo reverberations. Direct downhole measurement of the wall's sound speed can be made from the wall thickness and the time between within-wall pulse peak reverberations. The wall speed is one parameter used to calculate the density of whatever fluid is in contact with the wall. Another factor in calculating fluid density is the wall density but changes in the wall's density with temperature and pressure are a much smaller effect that can usually be ignored or estimated from a table.

The smooth data plot 34 comprises reflected signals both from signal reverberations within the near wall (between the first and second wall 24 and 26) as well as a reflection from the far wall (third wall 28). These reflected signals are illustrated as curves 36 on the smooth data plot 34. The acoustic signal reverberating within the near wall decays over time, this can be seen in the decreasing local maxima of the curves 36 of the smooth data plot 34 of FIG. 3. However, the amplitude of the signal reflected from the far wall (third wall 28) will exceed the amplitude of the last observable within-wall reverberation. Based on this, the variable threshold method can be used to determine the time (channel number) at which the far wall reflection pulse reaches its peak energy. Conceptually, the threshold keeps being lowered to the height of the last within-wall reverberation peak. The first pulse peak whose amplitude increases from its predecessor is taken as the far wall reflection.

In an embodiment of the present method, the variable pulse-peak-detection threshold function is generated using two passes. On the first pass, the threshold value for each channel is the largest energy (first derivative of CSS) value that occurred in the previous M channels, where M is the number of channels between peaks of energy pulses reverberating within the wall. This first pass for creating a variable threshold generates a staircase-like function (not shown) having horizontal steps joined by rises and falls that are not perfectly vertical. A graphical representation of the second pass is shown comprising a series of steps 40 having horizontal steps 42 and vertical sections 44. The vertical sections 44 are adjusted to be substantially vertical (i.e. have an infinite slope) while keeping the horizontal steps 42 substantially the same except for extending them left or right. This is accomplished by extending each horizontal step 42 leftward to the last channel of a higher step whenever a higher step 42 lies to its left.

Similarly, when a higher step lies to the right of an adjacent lower step, the lower step is extended rightward to the first channel of the higher step. Completion of the second pass generates a variable threshold that looks like a staircase whose vertical sections have a substantially infinite slope. Since the peaks of the inner-wall reverberation pulses get smaller over time, the first pulse whose peak increases over its predecessor's peak must be the signal that is reflected from the far wall (third wall 28). Accordingly, fluid sound speed is twice the fluid-filled gap distance divided by the round trip time between the first within-wall reverberation and the far-wall reflection. One of the many advantages of the ability to distinguish between signals representing near wall reverberations and signals that represent far wall reflections is that the signal generator 21 can be positioned within the confines of the vessel or container 20, on its outer circumference, or even within the body of the container 20 (i.e. between the first and second walls 24 and 26 or between the third and fourth walls 28 and 30).

The accuracy of the disclosed method is dependent on the accuracy of the measurement of the set of measured properties. It is desirable for the measured properties to consist of properties for which highly accurate measurements are available downhole to reduce propagation of uncertainty in the characterization of the desired property. For example, the sound speed of live oil at borehole temperatures and pressures is generally between 1100 and 1700 m/sec. Therefore, it is desirable to have a sound speed measurement resolution of near 1 meter per second, which is less than 0.1% of the typical sound speed value, to minimize uncertainty in the characterization of the desired fluid property.

It is to be understood that the methodology in accordance with the presently disclosed embodiments of the invention is readily practiced using current state-of-the-art computer systems, including, by way of example but not limitation, a Windows®-based "personal" or "PC" class of computers, such as are widely available from any number of commercial sources. Such a computer would preferably include, without limitation, a processor or processors capable of executing one or more applications suitable for performing the mathematical computations described herein, a mass data storage device accessible by the processor(s) for storing input data and calculated data in accordance with the present invention, and a user interface for permitting user control and operation of the overall system to achieve the results described herein. The selection of particular computer system hardware and software is not believed to be of particular relevance to the understanding and practice of the invention, so long as it meets the general criteria just stated. Those of ordinary skill in the art will undoubtedly be aware of numerous computer systems, associated application software, and/or combinations thereof suitable for the purposes of practicing the invention as disclosed herein.

From the foregoing detailed description, it should be apparent that a system and method for characterizing subsurface hydrocarbon formations using chemometric approach, allowing the practitioner to derive useful information from practically available data, thereby simplifying an otherwise highly complex process while attaining suitably accurate results.

Although specific embodiments of the invention have been described herein, it is to be understood that this has been done solely for the purposes of illustrating various features and aspects of the invention, and is not intended to be limiting with respect to the scope of the invention, as defined in the claims. It is contemplated and to be understood that various substitutions, alterations, and/or modifications, including such implementation variants and options as may have been specifically noted or suggested herein, may be made to the disclosed embodiment of the invention without departing from the spirit or scope of the invention.

The invention claimed is:

1. A method for characterizing a dissolved gas-liquid ratio of a fluid downhole using a correlation equation expressing the dissolved gas-liquid ratio in terms of at least sound speed, wherein the correlation equation was derived chemometrically from a training data set prepared by generating a plurality of output values from a plurality of input values to a set of multiple simultaneous existing correlation equations, the method comprising:
   receiving at least one input signal representing sound speed of a fluid downhole;
   processing the input signal with a computer using the correlation equation expressing the dissolved gas-liquid ratio in terms of at least sound speed wherein an output signal representing the dissolved gas-liquid ratio is produced; and
   outputting the output signal.

2. The method of claim 1, wherein the dissolved gas-liquid ratio is gas oil ratio.

3. The method of claim 1, wherein the dissolved gas-liquid ratio is gas brine ratio.

4. The method of claim 1, wherein the set of multiple simultaneous existing correlation equations comprise the Batzle and Wang relations.

5. The method of claim 1, wherein the input values comprise randomly-generated values corresponding to a plurality of fluid properties each within their expected range.

6. The method of claim 1, wherein the correlation equation was derived chemometrically using a regression.

7. The method of claim 1, wherein the correlation equation was derived chemometrically using a neural network analysis.

8. The method of claim 5, wherein the input values comprise:
   values for parameters which are measured downhole and
   values for parameters which are not measured downhole.

9. The method of claim 5, wherein the output values comprise:
   values for parameters which are measured downhole and
   values for parameters which are not measured downhole.

10. The method of claim 1, wherein the correlation equation expressing the dissolved gas-liquid ratio in terms of the sound speed has a correlation coefficient of at least 0.9.

11. The method of claim 1, wherein:
   the receiving comprises receiving a plurality of input signals representing a plurality of measured properties of a fluid downhole, wherein at least one measured property is sound speed; and
   the processing comprises processing the plurality of input signals using the correlation equation expressing the dissolved gas-liquid ratio in terms of the plurality of measured properties wherein an output signal representing the dissolved gas-liquid ratio is produced.

12. The method of claim 11, wherein the dissolved gas-liquid ratio is gas oil ratio.

13. The method of claim 11, wherein the dissolved gas-liquid ratio is gas brine ratio.

14. The method of claim 11, wherein the set of multiple simultaneous existing correlation equations comprise the Batzle and Wang relations.

15. The method of claim 11, wherein the training data set comprises randomly-generated values corresponding to a plurality of fluid properties.

16. The method of claim 11, wherein the correlation equation was derived chemometrically using a regression.

17. The method of claim 11, wherein the correlation equation was derived chemometrically using a neural network analysis.

* * * * *